(12) United States Patent
Blanchard

(10) Patent No.: US 11,168,297 B2
(45) Date of Patent: Nov. 9, 2021

(54) CELL MAINTAINER FOR AUTOLOGOUS CELL THERAPY PRODUCTION

(71) Applicant: Thrive Bioscience, Inc., Wakefield, MA (US)

(72) Inventor: Alan Blanchard, Middleton, MA (US)

(73) Assignee: Thrive Bioscience, Inc., Wakefield, MA (US)

( * ) Notice: Subject to any disclaimer, the term of this patent is extended or adjusted under 35 U.S.C. 154(b) by 78 days.

(21) Appl. No.: 15/563,360

(22) PCT Filed: Mar. 31, 2016

(86) PCT No.: PCT/US2016/025362
§ 371 (c)(1),
(2) Date: Sep. 29, 2017

(87) PCT Pub. No.: WO2016/161174
PCT Pub. Date: Oct. 6, 2016

(65) Prior Publication Data
US 2018/0079999 A1    Mar. 22, 2018

Related U.S. Application Data

(60) Provisional application No. 62/141,196, filed on Mar. 31, 2015.

(51) Int. Cl.
*C12M 3/00* (2006.01)
*C12M 1/00* (2006.01)
(Continued)

(52) U.S. Cl.
CPC ............ *C12M 37/04* (2013.01); *C12M 23/06* (2013.01); *C12M 23/16* (2013.01); *C12M 23/24* (2013.01);
(Continued)

(58) Field of Classification Search
CPC ..................................................... C12M 37/04
(Continued)

(56) References Cited

U.S. PATENT DOCUMENTS 6,465,244 B1 *  10/2002  Annable ................. B01L 1/025
                                                            119/311
2002/0090320 A1    7/2002  Burrow et al.
(Continued)

FOREIGN PATENT DOCUMENTS

EP    1 471 138 A1    10/2004
JP    2003-052365 A    2/2003
(Continued)

OTHER PUBLICATIONS

Machine translation of JP 2010154792 A provided by Espacenet, Kikuchi et al., 2010 (Year: 2010).*
(Continued)

*Primary Examiner* — Holly Kipouros
(74) *Attorney, Agent, or Firm* — Wolf, Greenfield & Sacks, P.C.

(57) ABSTRACT

In some aspects, the invention relates to automated cell culture incubators and their methods of use. In one aspect, the disclosure provides cell culture incubators having an airlock chamber, a storage chamber and/or an internal chamber. In some aspects, the disclosure provides methods for producing autologous mammalian cell cultures.

10 Claims, 5 Drawing Sheets

(51) Int. Cl.
*C12M 1/34* (2006.01)
*C12M 1/36* (2006.01)
*G01N 35/00* (2006.01)
*C12M 1/12* (2006.01)
*C12M 3/06* (2006.01)
*C12M 1/04* (2006.01)
*C12M 1/26* (2006.01)

(52) U.S. Cl.
CPC ............ *C12M 23/28* (2013.01); *C12M 23/44* (2013.01); *C12M 23/50* (2013.01); *C12M 29/00* (2013.01); *C12M 33/00* (2013.01); *C12M 37/00* (2013.01); *C12M 37/02* (2013.01); *C12M 41/14* (2013.01); *C12M 41/36* (2013.01); *C12M 41/46* (2013.01); *C12M 41/48* (2013.01); *C12M 47/04* (2013.01)

(58) Field of Classification Search
USPC ....................................................... 435/303.1
See application file for complete search history.

(56) References Cited

U.S. PATENT DOCUMENTS

| | | | |
|---|---|---|---|
| 2006/0194193 A1 | 8/2006 | Tsuruta et al. | |
| 2010/0330651 A1* | 12/2010 | Venter ................... | C12M 23/44 435/243 |
| 2012/0092478 A1* | 4/2012 | Honda ................... | C12M 41/14 348/79 |
| 2012/0122138 A1* | 5/2012 | Randles ................. | C12M 23/14 435/29 |
| 2012/0164721 A1 | 6/2012 | Kobayashi et al. | |
| 2013/0130361 A1 | 5/2013 | Okano et al. | |
| 2014/0051156 A1 | 2/2014 | Miyake et al. | |
| 2015/0079584 A1 | 3/2015 | Gevaert et al. | |

FOREIGN PATENT DOCUMENTS

| | | | | |
|---|---|---|---|---|
| JP | 2003-174870 A | 6/2003 | | |
| JP | 2004-511788 A | 4/2004 | | |
| JP | 2004-321111 A | 11/2004 | | |
| JP | 2006-101781 A | 4/2006 | | |
| JP | 2006-174828 A | 7/2006 | | |
| JP | 3157029 U | 1/2010 | | |
| JP | 2010154792 A | * 7/2010 | ............ | C12M 37/00 |
| JP | 2012-130297 A | 7/2012 | | |
| JP | 2012-524268 A | 10/2012 | | |
| WO | WO 2012/098931 A1 | 6/2014 | | |

OTHER PUBLICATIONS

Colomb et al., Advantages of digital holographic microscopy for real-time full field absolute phase imaging, 2008, Proc. of SPIE vol. 6861 (Year: 2008).*

Buggenthin et al., An automatic method for robust and fast cell detection in bright field images from high-throughput microscopy, 2013, BMC Bioinformatics, 14:297, pp. 1-12 (Year: 2013).*

International Search Report and Written Opinion for Application No. PCT/US2016/025362 dated Sep. 9, 2016.

International Preliminary Report on Patentability for Application No. PCT/US2016/025362 dated Oct. 12, 2017.

Extended European Search Report for Application No. EP 16774245.1 dated Feb. 20, 2019.

U.S. Appl. No. 17/225,944, filed Apr. 8, 2021, Blanchard.

\* cited by examiner

CELL MAINTAINER FOR AUTOLOGOUS CELL THERAPY PRODUCTION

RELATED APPLICATIONS

This application is a National Stage Application of PCT/US2016/025362, filed Mar. 31 2016, entitled "Cell Maintainer For Autologous Cell Therapy Production", which claims the benefit under 35 U.S.C. § 119(e) of U.S. provisional application. U.S. Ser. No. 62/141,196, filed Mar. 31, 2015, and entitled "Cell Maintainer For Autologous Cell Therapy Production", the entire disclosure of each of which is incorporated by reference herein.

FIELD

Aspects relate to automated cell culture incubators and to methods for using such incubators. Some aspects relate to methods for producing autologous mammalian cell cultures.

BACKGROUND

Autologous cell therapy is a personalized medicine technique in which human cells are implanted, transplanted, infused, or transferred back into the individual from whom the cells or tissue were originally recovered. For example, chondrocytes may be isolated from a patient having a cartilage injury, expanded in a culture system and then implanted back into the patient for the purposes of alleviating joint pain associated with the cartilage injury. Other examples of autologous cell therapies include autologous dendritic cells, mesenchymal stromal cells and T lymphocytes. Autologous cell therapies have many advantages including immediate donor availability, reduced cell or tissue rejection, and reduced graft-versus-host disease. Additionally, the autologous nature of the cells means there is no need for HLA matching and immunosuppression of the cell recipient. Although there are many therapeutic advantages of autologous cell therapy, several challenges in the manufacturing and production of autologous cell cultures impose barriers to commercial success.

SUMMARY

One challenge for the manufacturing autologous cell therapies is "scale-out", or the ability to simultaneously produce multiple batches of autologous cell cultures from different donors. Strict aseptic conditions must be maintained in order to prevent cross-contamination between autologous cultures from different patients. Some currently used methods and devices for autologous cell culture rely on manual culture techniques, which can introduce contaminants to cultures and expose cultures to non-aseptic conditions and/or variations of the physical environment (e.g., changes in temperature, humidity, etc., or any combination thereof). Other cell culture apparatus do not provide the ability to culture cells from multiple donors with minimal risk of cross-contamination. Accordingly, new cell culture systems and methods are provided herein that permit remote maintenance and significant scale-out capabilities of multiple cell cultures while maintaining stringent aseptic conditions.

In some aspects, this document provides a method for producing a mammalian cell culture that include: (a) introducing a mammalian cell sample into a cell culture vessel in the presence of growth media, wherein the vessel includes a passage configured to permit materials to be aseptically transferred into or out of the vessel; and, (b) expanding the cell sample in an incubator into a mammalian cell culture, wherein the incubator comprises a sterile inner growth chamber.

In some embodiments, the cell sample is introduced into the cell culture vessel through the passage. In some embodiments, the passage of the vessel is covered by a gas-permeable membrane. In some embodiments, a membrane on a culture vessel provides a one-way valve or "environmental" interface through which the gaseous environment may be controlled within the closed, autologous culture vessel. In some embodiments, multiple closed systems (e.g., within a single, temperature controlled environment) may be provided in the form of a plurality of autologous culture vessels. In some embodiments, an overall incubator environment maintains the environmental temperature of the collective system. In some embodiments, the internal gaseous environment of each closed vessel is maintained through an interface (e.g., a plumbing interface) which contains a set of membrane "valves" for gas exchange. In such embodiments, this configuration facilitates control, monitoring and documentation of independent autologous cultures.

In some embodiments, the method further comprises aseptically introducing growth media to the cell culture through the passage in the vessel.

In some embodiments, the method further comprises aseptically introducing a biological material to the cell culture through the opening in the vessel. In some embodiments, the biological material is a cell growth factor. In some embodiments, the biological material is a nucleic acid molecule. In some embodiments, the nucleic acid molecule is a nucleic acid vector. In some embodiments, the nucleic acid vector is a transfection vector. In some embodiments, the nucleic acid vector is a transduction vector. In some embodiments, the nucleic acid vector comprises transgenic material. In some embodiments, the biological material is an enzyme (e.g., a nuclease, a ligase, a polymerase, or other enzyme that modifies a nucleic acid). In some embodiments, the biological material comprises a mixture of nucleic acid modifying enzyme(s) and one or more nucleic acids.

In some embodiments, the methods further comprise aseptically monitoring conditions of the growth media. In some embodiments, the incubator is maintained at a constant temperature range. In some embodiments, the incubator is maintained at about 37 degrees Celsius.

In some embodiments, the methods further comprise aseptically monitoring conditions of the cell.

In some embodiments, the methods further comprise aseptically adding reagents to control the chemical composition of the growth media (e.g., the pH, the concentration of glucose, the concentration of lactate, the concentration of other small molecules, or the overall osmolality of the growth media).

In some embodiments, the methods further comprise aseptically imaging the cell culture. In some embodiments, the method further comprises filtering the cell culture. In some embodiments, the method further comprises aseptically removing an aliquot of the cell culture. In some embodiments, the incubator is a cell culture system as described herein.

In some aspects, this document provides a cell culture system comprising an incubator cabinet comprising: a transfer chamber; one or more internal chambers; an external door opening from an external environment to the transfer chamber; a first internal door opening from the transfer chamber to a first internal chamber; a second internal door opening from the transfer chamber to a second internal chamber; and a transfer device for moving one or more items between the transfer chamber and the first internal chamber, and/or between the transfer chamber and the second internal chamber and/or between the second internal chamber and the first internal chamber.

In some embodiments, the cell culture system further comprises a sterilization medium supply (e.g., an ozone generator) coupled to a pump, wherein the sterilization medium supply (e.g., the ozone generator) is configured for supplying sterilization medium (e.g., ozone gas) to the transfer chamber. In some embodiments, the sterilization medium supply (e.g., ozone generator) is configured for supplying sterilization medium (e.g., ozone gas) to the one or more internal chambers.

In some embodiments, the external door forms a substantially gas-tight seal when closed. In some embodiments, the first internal door and the second internal door each forms a substantially gas-tight seal when closed.

In some embodiments, the pump is configured to remove sterilization medium from the transfer chamber and/or one or more internal chambers.

In some embodiments, the storage chamber comprises a storage location. In some embodiments, the storage location is configured to hold a plurality of cell culture vessels. In some embodiments, each vessel of the plurality of cell culture vessels contains cells from a different patient. In some embodiments, each vessel of the plurality of cell culture vessels is tagged with a unique barcode.

In some embodiments, the internal chamber comprises an imager and an imaging location. In some embodiments, the imager is a holographic imager. In some embodiments, the imager is a microscope, such as a bright-field microscope or a fluorescence microscope. In some embodiments, the cell culture system further comprises a controller for the imager.

In some embodiments, the internal chamber comprises a manipulator and a manipulation location. In some embodiments, the manipulator is a cell picker. In some embodiments, the manipulator comprises a fluid handling system.

In some embodiments, the cell culture system further comprises a controller for the manipulator.

In some embodiments, the internal chamber comprises a fluid storage location. In some embodiments, the internal chamber comprises a cell sorting or cell isolation apparatus. In some embodiments, the cell sorting or cell isolation apparatus is a centrifuge. In some embodiments, the cell sorting or cell isolation apparatus is a Fluorescence-Activated Cell Sorting (FACS) machine. In some embodiments, the internal chamber comprises a microfluidic device for imaging and/or manipulating individual cells.

In some embodiments, the transfer device comprises one or more robotic elements. In some embodiments, the cell culture system further comprises a controller for the transfer device. In some embodiments, the controller for the imager, the controller for the manipulator, and/or the controller for the transfer device are external to the incubator cabinet. In some embodiments, the controller for the imager, the controller for the manipulator and/or the controller for the transfer device comprises a single processor. In some embodiments, the controller for the imager, the controller for the manipulator, and/or the controller for the transfer device comprise a computer. In some embodiments, a single computer controls the imager, the manipulator, and/or the transfer device.

In some embodiments, the cell culture system further comprises a barcode scanner. In some embodiments, the barcode scanner is connected to a computer, wherein the computer is external to the incubator cabinet.

In some aspects, this document provides a cell culture system comprising two or more cell culture vessels, wherein each vessel comprises cells from a different patient and wherein each vessel comprises a passage configured to permit materials to be aseptically passed into or out from the vessel.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. Various embodiments of the invention will now be described, by way of example, with reference to the accompanying drawings, in which:

FIG. 2A shows a schematic of a cell culture system comprising an incubator cabinet comprising a transfer chamber and an internal chamber; FIG. 2B shows a schematic of a cell culture incubator comprising an incubator cabinet comprising a transfer chamber, an internal chamber containing a plurality of cell culture vessels, an ozone generator, and a pump;

DETAILED DESCRIPTION

Figure 1:
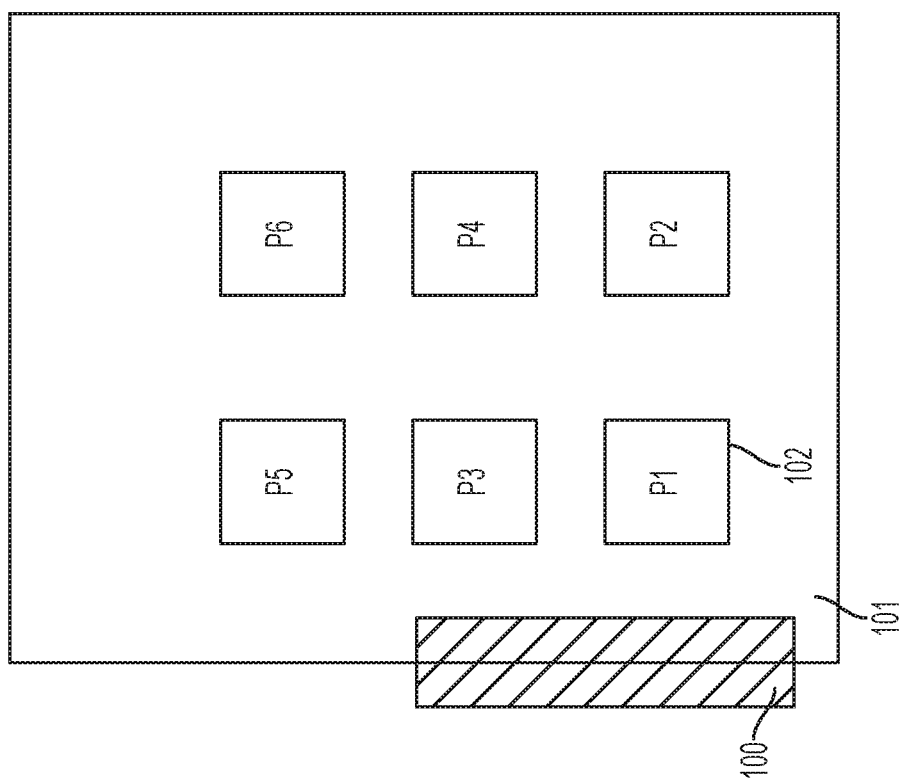
FIG. 1 is a schematic of an illustrative embodiment of a cell culture system comprising an incubator cabinet comprising an internal chamber containing a plurality of cell culture vessels. Each cell culture vessel contains a cell culture from a different subject.

Currently used cell culture incubators impose barriers to the success of autologous cell culture. For example, many cell culture incubators require the removal of cell culture vessels and their subsequent manual handling. Removal of cultured cells from the protected environment provided by an incubator increases exposure of the culture to potential contaminants, including cross-contamination from other autologous cell cultures, and/or variations of the physical environment (e.g., changes in temperature, humidity, etc., or any combination thereof). Furthermore, manual handling of cultures by human operators introduces the possibility of contamination introduced by human error, such as improper sterile technique. The methods and apparatus for remote maintenance (e.g., with minimal human handling) of autologous cell cultures in this document overcome these barriers and issues. This document is based, in part, on development of cell culture vessels that have the capability to allow aseptic passage of materials into and out of the cell culture vessel and to allow the simultaneous production of a plurality of cell cultures from different subjects while minimizing risk of cross-contamination between the cultures and the exposure of the culture to a non-aseptic and/or non-controlled physically environment.

Cell Culture Methods

In one aspect, this document relates to a method for producing a mammalian cell culture including the steps of introducing a mammalian cell sample into a cell culture vessel in the presence of growth media, wherein the vessel has a passage configured to permit materials to be aseptically passed into or out from the vessel; and expanding the cell sample in an incubator into a mammalian cell culture, wherein the incubator includes a sterile internal chamber.

As used herein, "cell culture" refers to a procedure for maintaining and/or growing cells under controlled conditions (e.g., ex vivo). In some embodiments, cells are cultured under conditions to promote cell growth and replication, conditions to promote expression of a recombinant product, conditions to promote differentiation (e.g., into one or more tissue specific cell types), or a combination of two or more thereof.

As used herein, the term "mammalian cell sample" refers to any cell obtained from a mammalian subject. Non-limiting examples of mammalian subjects include humans, non-human primates, mice, rats, horses, dogs, cats, and guinea pigs. In some embodiments, the mammalian cell sample is obtained from a human.

In some embodiments, a cell sample is isolated from a tissue or organ (e.g., a human tissue or organ), including but not limited to solid tissues and organs. In some embodiments, cell samples can be isolated from placenta, umbilical cord, bone marrow, liver, blood, including cord blood, or any other suitable tissue. In some embodiments, patient-specific cell samples are isolated from a patient for culture (e.g., for cell expansion and optionally differentiation) and subsequent re-implantation into the same patient or into a different patient. In some embodiments, cells grown in an incubators described herein may be used for allogenic or autogeneic therapy. In some embodiments, cells grown in the incubators disclosed herein may be genetically modified, expanded and reintroduced into a patient for the purpose of providing an immunotherapy (e.g., chimeric antigen receptor therapy (CAR-T), or delivery of CRISPR/Cas modified cells).

In some embodiments, cells are isolated from tissues or biological samples for ex vivo culture in an incubator described herein. In some embodiments, cells (e.g., white blood cells) are isolated from blood. In some embodiments, cells are released from tissues or biological samples using physical and/or enzymatic disruption. In some embodiments, one or more enzymes such as collagenase, trypsin, or proteinase are used to digest the extracellular matrix. In some embodiments, tissue or biological samples are placed in culture medium (e.g., with or without physical or enzymatic disruption), and cells that are released and that grow in the culture medium can be isolated for further culture.

The methods described herein are suitable for culturing a variety of mammalian cell types. In some embodiments, the mammalian cell sample is a cell useful for autologous cell therapy. As used herein, the term "autologous cell therapy" refers to the implantation, transplantation, infusion, or transfer of cultured cells back into the individual from whom the cells were obtained. For example, immune cells may be obtained from a subject having cancer, expanded into a cell culture, primed with an antigen against the cancer, and reintroduced into the patient in order to boost the subject's immune response. Examples of cells that are useful for autologous culture include but are not limited to, stem cells (e.g., hematopoietic stem cells, somatic stem cells, totipotent stem cells, pluripotent stem cells, fetal stem cells, embryonic stem cells, mesenchymal stem cells, and induced pluripotent stem cells), progenitor cells (e.g., satellite cells, neural progenitor cells, bone marrow stromal cells, pancreatic progenitor cells, angioblasts and endothelial progenitor cells), immune cells (e.g., T-lymphocytes, dendritic cells) and differentiated cells (epithelial cells, cardiomyocytes, fibroblasts, and chondrocytes).

As described herein passages can be configured to permit aseptic transfer of materials into and out of a vessel in a manner that is useful for minimizing cross-contamination during the simultaneous culture of mammalian cells from different subjects. In some aspects, the methods provided herein relate to using a cell culture vessel, wherein the vessel includes a passage configured to permit materials to be aseptically transferred into or out from the vessel. As used herein, the term "passage" refers to a conduit that allows the movement of materials into or out of the vessel. For example the vessel may be an open-ended tube that is sealed at its opening by a pierceable, self-sealing membrane. In some embodiments, the membrane is a gas-permeable membrane. In some embodiments, the passage is a sterile, disposable tube in fluid communication with a sealed, gas-permeable vessel. In some embodiments, the passage is a network of microfluidic channels, having inlet and outlet ports capable of being sterilized, that are integrated into a sealed culture vessel.

As used herein, the term "aseptically transferred" refers to the movement of material from one location to another without the introduction of contaminants. For example, it may be desirable that culture media is aseptically transferred from a storage container to a cell culture vessel because non-aseptic transfer of the media could introduce pathogens or other contaminants into the cell culture. Contaminants include but are not limited to bacteria (e.g. pathogenic bacteria and non-pathogenic bacteria), viruses (e.g. pathogenic viruses and non-pathogenic viruses), molds, spores, and dust. In some embodiments, a contaminant is a cell. For example, when cells obtained from different subjects are simultaneously cultured, aseptic transfer of materials is required so that cross-contamination (i.e., the introduction of a cell or media from one culture to a different culture) does not occur.

Aseptic techniques can be used to prevent or minimize contamination of cell cultures during growth and manipulation. In some embodiments equipment (e.g., pipettes, fluid handling devices, manipulating devices, other automated or robotic devices, etc.) that is used for cell culture is sterilized using an appropriate technique. Non-limiting techniques include heat exposure (e.g., autoclaving), surface disinfection (e.g., using alcohol, bleach, or other disinfectant), irradiation, and/or exposure to a disinfectant gas (e.g., ozone, hydrogen peroxide, etc.) as described herein. In some embodiments, media is sterilized using an appropriate technique. Non-limiting techniques include heat exposure (e.g., autoclaving), antimicrobial/antiviral treatment, filtration, and/or irradiation.

In some embodiments, manipulations of cell cultures are performed under aseptic conditions, for example, in an environment (e.g., within an incubator chamber) that has been disinfected and in which the air has been filtered to remove potential contaminants.

In some embodiments, cell cultures are grown and maintained under GMP-compliant conditions, including those that include using GMP-compliant media or GMP-compliant liquid handling equipment. In some cases, cell cultures are grown and maintained by performing methods in conjunction with standard operation procedures (SOPs).

In some embodiments, cell cultures can be monitored and/or evaluated to detect contamination. In some embodiments, contamination by cells from a different type of organism can be detected. In some embodiments, contamination of a mammalian cell culture by *mycoplasma*, bacteria, yeast, or viruses can be detected using any suitable technique. In some embodiments, cell culture contamination can be detected by assaying for changes or for rates of change of one or more culture properties such as pH, turbidity, etc., that are characteristic of contamination (e.g., by bacteria or yeast) and not characteristic of the cells (e.g., mammalian cells) being grown in culture. In some embodiments, one or more molecular detection assays (e.g., PCR, ELISA, RNA labeling, or other enzymatic techniques) or cell-based assays can be used to detect contamination (e.g., *mycoplasma*, bacterial, yeast, viral, or other contamination).

In some embodiments, cell cultures can be monitored and/or evaluated to detect contamination with cells of similar types (e.g., a human cell line contaminated by different human cells or by different mammalian cells). In some embodiments, cell cultures and their potential contamination can be evaluated using DNA sequencing or DNA fingerprinting (e.g., short tandem repeat—STR—fingerprinting), isoenzyme analysis, human lymphocyte antigen (HLA) typing, chromosomal analysis, karyotyping, cell morphology, or other techniques.

In some embodiments, cells produced using the incubators or methods described herein can be frozen to preserve them for later use and/or for transport. In some embodiments, cells are mixed with a cryopreservation composition after growth and/or differentiation and prior to freezing. A cryopreservation composition can be added to a cell culture vessel, or cells can be transferred from a cell culture vessel to a cryopreservation vessel along with a cryopreservation composition. Non-limiting examples of cryoprotectants that can be included in a cryopreservation composition include DMSO, glycerol, PEG, sucrose, trehalose, and dextrose. In some embodiments, a freezer may be provided as a component of an incubator to facilitate freezing of cells isolated from cell cultures. For example, one or more freezers may be located in an internal chamber and/or integrated into the incubator cabinet (e.g., into a wall of the incubator cabinet).

As used herein, a "cell culture vessel" is a device including a housing and one or more chambers for culturing cells. In some embodiments, the housing is a frame. The frame may be coupled to a lid. The one or more chambers may include cell culturing media including one or more membranes. In some embodiments, a cell culture vessel may include nutrients for promoting the growth of cells. In certain embodiments, a cell culture vessel may entirely enclose one or more cells or groups thereof. The housing of a cell culture vessel may include one or more pores or openings to permit the transfer of gases between a cell culture vessel and its surrounding environment. In certain embodiments, a cell culture vessel includes a transparent or optically clear window. For example, a lid coupled to the housing of a cell culture vessel may include an optically clear portion for viewing cells e.g., with a microscope or other imager.

Various types of cell culture vessels can be designed as described herein. Cell culture vessels can be made from any non-reactive biocompatible material, such as glass, plastic or silicone. Generally, cell culture vessels are formed into bottles, flasks, vials, bags, tubes or culture plates. In some embodiments, the cell culture vessel is a vial. In some embodiments, the cell culture vessel is a bottle or flask. In some embodiments, the cell culture vessel is a culture plate. In some embodiments, the plate is a cell culture dish. In some embodiments, the plate is a multi-well culture plate. Generally multi-well plates include an array of 96, 384 or 1536 wells. In some embodiments, a cell culture vessel includes one or more portions that are substantially non-reflective. In some embodiments, the cell culture vessel is barcoded. In some embodiments, an incubator includes a barcode reader.

In some embodiments, cell culture vessels may be pre-kitted with one or more reagents desired for a particular purpose, e.g., for growing cells, for differentiating cells, for subjecting cells to a particular assay condition, etc. In some embodiments, pre-kitted cell culture vessels contain reagents useful for performing a particular experiment (e.g., cell growth media, growth factors, selection agents, labeling agents, etc.) on a cell culture, in advance of the experiment. Pre-kitted cell culture vessels may facilitate experimental protocols by providing cell culture-ready vessels that do not require the addition of reagents. For example, progenitor cells from a patient may be added to a cell culture vessel pre-kitted with reagents for cell differentiation for the purpose of expanding a population of differentiated cells for autologous cell therapy. Pre-kitted cell culture vessels can be stored at any appropriate temperature, which is determined by the recommended storage parameters of the reagents within the pre-kitted cell culture vessel. In some embodiments, pre-kitted cell culture storage vessels are stored prior to use at temperatures between about −80° C. and about 37° C. In some embodiments, pre-kitted cell culture storage vessels are stored prior to use at temperatures between about −80° C. and about −20° C. In some embodiments, pre-kitted cell culture storage vessels are stored prior to use at temperatures between about −20° C. and about 4° C. In some embodiments, pre-kitted cell culture storage vessels are stored prior to use at temperatures between about 4° C. and about 37° C. In some embodiments, pre-kitted cell culture vessels are disposable. In some embodiments, pre-kitted cell culture vessels are reusable and/or refillable.

In some embodiments, cell culture vessels are configured for culturing cells in suspension. In some embodiments, cell culture vessels are configured for culturing adherent cells. In some embodiments, cell culture vessels are configured for 2D or 3D cell culture. In some embodiments, cell culture vessels include one or more surfaces or micro-carriers to support cell growth. In some embodiments, these are coated with extracellular matrix components (e.g., collagen, fibrin and/or laminin components) to increase adhesion properties and/or to provide other signals needed for growth and differentiation. In some embodiments, cell culture vessels include one or more synthetic hydrogels such as polyacrylamide or polyethylene glycol (PEG) gels to support cell growth. In some embodiments, cell culture vessels include a solid support with embedded nutrients (e.g., a gel or agar, for example for certain bacterial or yeast cultures). In some embodiments, cell culture vessels include a liquid culture medium.

In some embodiments, growth media is aseptically introduced into the cell culture vessel. As used herein, the term "growth media" refers to a medium for culturing cells containing nutrients that maintain cell viability and support proliferation. In some cases various parameters and conditions can be used for culturing cells. The growth media may contain any of the following nutrients in appropriate amounts and combination: salt(s), buffer(s), amino acids, glucose or other sugar(s), antibiotics, serum or serum replacement, and other components such as peptide growth factors, etc. Growth media are known in the art and may be classified as natural or artificial media. Examples of cell culture media include but are not limited to Minimum Essential Medium (MEM), Dulbecco's Modified Eagle's Medium (DMEM), and Roswell Park Memorial Institute Medium (RPMI). An appropriate medium for culturing the cell may be selected.

In some embodiments, cells are cultured in one of any suitable culture media. Different culture media having different ranges of pH, glucose concentration, growth factors, and other supplements can be used for different cell types or for different applications. In some embodiments, custom cell culture media or commercially available cell culture media such as Dulbecco's Modified Eagle Medium, Minimum Essential Medium, RPMI medium, HA or HAT medium, or other media available from Life Technologies or other commercial sources can be used. In some embodiments, cell culture media include serum (e.g., fetal bovine serum, bovine calf serum, equine serum, porcine serum, or other serum). In some embodiments, cell culture media are serum-free. In some embodiments, cell culture media include human platelet lysate (hPL). In some embodiments, cell culture media include one or more antibiotics (e.g., actinomycin D, ampicillin, carbenicillin, cefotaxime, fosmidomycin, gentamycin, kanamycin, neomycin, penicillin, penicillin streptomycin, polymyxin B, streptomycin, tetracycline, or any other suitable antibiotic or any combination of two or more thereof). In some embodiments, cell culture media include one or more salts (e.g., balanced salts, calcium chloride, sodium chloride, potassium chloride, magnesium chloride, etc.). In some embodiments, cell culture media include sodium bicarbonate. In some embodiments, cell culture media include one or more buffers (e.g., HEPES or other suitable buffer). In some embodiments, one or more supplements are included. Non-limiting examples of supplements include reducing agents (e.g., 2-mercaptoethanol), amino acids, cholesterol supplements, vitamins, transferrin, surfactants (e.g., non-ionic surfactants), CHO supplements, primary cell supplements, yeast solutions, or any combination of two or more thereof. In some embodiments, one or more growth or differentiation factors are added to cell culture media. Growth or differentiation factors (e.g., WNT-family proteins, BMP-family proteins, IGF-family proteins, etc.) can be added individually or in combination, e.g., as a differentiation cocktail including different factors that bring about differentiation toward a particular lineage. Growth or differentiation factors and other aspects of a liquid media can be added using automated liquid handlers integrated as part of an incubator provided herein.

In some embodiments, biological material is aseptically introduced into the cell culture vessel. Examples of biological materials include but are not limited to growth factors, nucleic acids, and expression vectors. Growth factors are naturally occurring substances that stimulate cell growth, proliferation, healing and/or differentiation. Generally, growth factors are proteins or steroid hormones. In the context of mammalian cell culture, growth factors may be introduced to culture media in order to control the cell cycle or induce proliferation or differentiation of cultured cells. Non-limiting examples of growth factors include angiopoietin, bone morphogenic proteins (BMPs), epidermal growth factor (EGF), brain-derived neurotrophic factor (BDNF), erythropoietin (EPO), fibroblast growth factor (FGF), granulocyte colony-stimulating factor (G-CSF), insulin-like growth factor (IGF), nerve growth factor (NGF), transforming growth factor beta (TGF-β), and vascular endothelial growth factor (VEGF).

In some embodiments, the biological material is a nucleic acid or expression vector. For example, somatic cells can be "reprogrammed" to become induced stem cells via the introduction of genetic material encoding reprogramming protein factors and microRNA. In some embodiments, the methods provided herein further included aseptic introduction of a nucleic acid or expression vector into the cell culture vessel. In some embodiments, a nucleic acid is introduced to the cell culture. Examples of nucleic acids include DNA, RNA, siRNA, miRNA, ami-RNA, shRNA, and dsRNA. In some embodiments, an expression vector is introduced into the cell culture vessel. The term "expression vector" refers to an engineered molecule capable of artificially carrying foreign genetic material into another cell and expressing the genetic material in the cell. Expression vectors can generally be classified as transfection vectors and transduction vectors. Transfection vectors (e.g., DNA-based plasmid vectors) are generally used for non-virally-mediated transfer of genetic material into cells. Transduction vectors (e.g., lentivital vectors, AAV vectors, rAAV vectors, and retroviral vectors) are generally used for virally-mediated transfer of genetic material into cells. In some embodiments, the expression vector includes a transgene. The composition of the transgene sequence of an expression vector will depend upon the use to which the resulting vector will be put. For example, one type of transgene sequence includes a reporter sequence, which upon expression produces a detectable signal. In another example, the transgene encodes a therapeutic protein or therapeutic functional RNA.

In some aspects, this documents relates to methods for monitoring cells under controlled conditions (e.g., under aseptic and/or sterile conditions). In some aspects, methods described herein are useful for cell culture (e.g., to grow and maintain cells for recombinant protein expression or to grow and/or differentiate cells for therapeutic applications such as implantation). In some embodiments, the conditions (e.g., environment) inside incubators provided herein are monitored. In some cases, the temperature, humidity, carbon dioxide, oxygen and other gaseous components inside the incubator may be monitored. In some embodiments, the conditions (e.g., temperature, oxygen, carbon dioxide, and pH) of the growth media are monitored. Growth media conditions can be monitored directly, via probes and sensors, or indirectly via colorimetric (e.g., media containing Phenol Red) or imaging techniques (e.g., infrared or thermal imaging). In some embodiments, conditions of growth media and cells are monitored by aseptically removing an aliquot contains growth media and cells from a culture vessel and analyzing the aliquot at a location external to the culture vessel. In some embodiments, the aliquot is filtered, for example, by centrifugation to separate the cells from the growth media.

In some embodiments, incubators and methods described herein are used to monitor or assay culture media for nutrient depletion, changes in pH, changes in temperature, accumulation of apoptotic or necrotic cells, and/or cell density. In some embodiments, incubators and methods described herein are used to modify or change the culture media or conditions and/or to passage the cell cultures when appropriate. In some embodiments, the methods described herein are automated.

Cell Culture Systems

In some aspects, this document relates to cell culture systems including an incubator cabinet. As used herein, an "incubator cabinet" is a housing that includes one or more chambers configured to hold one or more cell culture vessels. In some embodiments, an incubator cabinet includes a transfer chamber and an internal chamber, one or both of which are configured to hold one or more cell culture vessels. In some embodiments, an incubator may include one or more other elements such as one or more gas sources (e.g., a gas cylinder or ozone generator), tubing (e.g., to convey one or more liquids or gases such as water, distilled water, deionized water, cell culture medium, air, carbon dioxide, ozone, and oxygen), airflow mechanisms (e.g., valves, release valves, pinholes, gas regulators, and mass flow regulators), pressure mechanisms (e.g., a pump such as a dry scroll pump, rotary pump, momentum transfer pump, diffusion pump, or diaphragm pump; a suction tube; a vacuum system; and an air blower), environmental monitors and controls (e.g., a gas sensor and/or monitor to sense and/or control concentrations of gases such as carbon dioxide, oxygen, and ozone; heat sources or sinks; temperature monitors and controls; humidity monitors; gas scrubbers; air filters; instrumentation for measuring particulate matter; pressure gauges; and flow meters), doors (e.g., openings or panels), windows (e.g., optical windows made of glass, plastic, composite, or other substantially transparent material for viewing an area inside the incubator cabinet), ports (e.g., to permit the introduction or removal of one or more gases or liquids), light sources (e.g., lamps, bulbs, lasers, and diodes), optical elements (e.g., microscope objectives, mirrors, lenses, filters, apertures, wave plates, windows, polarizers, fibers, beam splitters, and beam combiners), imaging elements (e.g. cameras, barcode readers), electrical elements (e.g., circuits, cables, power cords, and power supplies such as batteries, generators, and direct or alternating current supplies), computers, mechanical elements (e.g., motors, wheels, gears, robotic elements, and actuators such as pneumatic actuators, electromagnetic actuators, motors with cams, piezoelectric actuators, and motors with lead screws), and control elements (e.g., spin-wheels, buttons, keys, toggles, switches, cursors, screws, dials, screens, and touchscreens). In some embodiments, one or more of these other elements are part of the incubator, but are external to the incubator cabinet. In some embodiments, one or more of these other elements are included within the incubator cabinet.

In some embodiments this document relates to incubators and methods for culturing, manipulating, and/or monitoring cells under controlled conditions (e.g., under aseptic and/or sterile conditions). In some embodiments, the cell culture incubators included an incubator cabinet having an internal chamber for incubation of cells in one or more cell culture vessels. In some cases, in addition to an internal door from the transfer chamber to the internal chamber, the incubators include at least one external door (e.g., 1, 2, 3, 4, or more external doors) opening from an external environment directly to the internal chamber, for example, to provide alternative access to the internal chamber during periods of time when the incubator is not operational, e.g., during maintenance of the incubator. In some embodiments, incubators include a storage location within the internal chamber for storing one or more cell culture vessels.

In some embodiments, incubators or incubator cabinets provided herein are rectangularly cuboidal in shape. In some embodiments incubators or incubator cabinets provided herein have a rectangular footprint in a range of 1 ft$^2$ to 16 ft$^2$. In some embodiments incubators or incubator cabinets provided herein have a rectangular footprint of up to about 1 ft$^2$, 2 ft$^2$, 3 ft$^2$, 4 ft$^2$, 5 ft$^2$, 6 ft$^2$, 7 ft$^2$, 8 ft$^2$, 9 ft$^2$, 10 ft$^2$, 11 ft$^2$, 12 ft$^2$, 13 ft$^2$, 14 ft$^2$, 15 ft$^2$, or 16 ft$^2$. In some embodiments incubators or incubator cabinets provided herein have a total chamber volume in a range of 1 ft$^3$ to 100 ft$^3$. In some embodiments incubators or incubator cabinets provided herein have a chamber volume of up to about 1 ft$^3$, 5 ft$^3$, 10 ft$^3$, 25 ft$^3$, 50 ft$^3$ or 100 ft$^3$. In some embodiments incubators or incubator cabinets provided herein have a rectangular footprint in a range of 0.09 m$^2$ to 1.78 m$^2$. In some embodiments incubators or incubator cabinets provided herein have a rectangular footprint of up to about 0.1 m$^2$, 0.2 m$^2$, 0.3 m$^2$, 0.4 m$^2$, 0.5 m$^2$, 0.6 m$^2$, 0.7 m$^2$, 0.8 m$^2$, 0.9 m$^2$, 1.0 m$^2$, 1.1 m$^2$, 1.2 m$^2$, 1.3 m$^2$, 1.4 m$^2$, 1.5 m$^2$, 1.6 m$^2$, or 1.7 m$^2$. In some embodiments, incubators or incubator cabinets provided herein have a total chamber volume in a range of 0.03 m$^3$ to 3 m$^3$. In some embodiments incubators or incubator cabinets provided herein have a chamber volume of up to about 0.03 m$^3$, 0.1 m$^3$, 0.3 m$^3$, 1 m$^3$, or 3 m$^3$.

In some embodiments, an incubator cabinet is single-walled. In some embodiments, an incubator is double-walled. In some embodiments, insulation material is provided between the double walls of an incubator cabinet to control heat loss from the cabinet and facilitate temperature control in the cabinet. In some embodiments, the outer wall of an incubator cabinet includes a sheet metal, e.g., a 14-20 gauge cold rolled steel. In some embodiments, an inner wall (e.g., a chamber surface) of an incubator cabinet includes electro-polished stainless steel. In some embodiments, an inner wall (e.g., a chamber surface) of an incubator cabinet includes corrosion resistant materials, such as, titanium, cobalt-chrome, tantalum, platinum, zirconium, niobium, stainless steel, and alloys thereof. However, in some embodiments, a chamber surface of an incubator cabinet includes a polymeric material such as polytetrafluoroethylene (PTFE), or a polymeric material know under the trade name of Parylene. In some embodiments, a chamber surface may have anti-microbial properties, such as copper or silver or anti-microbial compounds incorporated into a polymeric surface coating.

In some embodiments, the incubator includes an airlock arrangement that may be used to help decreases exposure of the internal chamber to the external environment, or exposure of the external environment to the internal chamber. For example, an incubator cabinet may include an external door leading to a transfer chamber and an internal chamber, wherein the transfer chamber and the internal chamber are physically separated by a wall having an internal door. In some embodiments, to utilize the airlock arrangement, one door is opened at a time. For example, an operator may open the external door to gain access to the transfer chamber. The operator may then insert item(s) such as pipette tips into the transfer chamber. An operator may operate the external door by directly manipulating the door. In some embodiments, an operator may operate the door indirectly by controlling the operation of the door remotely, e.g., through the use of automation configured to control opening and closing of the doors. In some embodiments, the internal chamber door remains closed while the external door is open. In some embodiments, after item(s) are inserted into the transfer chamber, the external door is closed (e.g., directly or indirectly by an operator). Once the external door is closed, a sterilization process inside the transfer chamber is used to sterilize the inserted item(s). Once sterilization is complete, the internal chamber door is opened, and the sterilized items are moved from the transfer chamber into the internal chamber (e.g., by one or more transfer devices).

In some embodiments, the transfer chamber and/or the internal chamber may have a gas-tight or hermetic seal, e.g., around one or more windows or doors. In particular embodiments, sealants such as grease and/or mechanical elements such as o-rings, gaskets, septa, KF, LF, QF, quick coupling, or other sealing mechanisms may be used to establish one or more gas-tight seals. In some embodiments, grooves, depressions, protrusions, and/or molded plastic elements may facilitate in establishing one or more gas-tight seals. In some embodiments, an incubator (e.g., an internal chamber, and/or a transfer chamber of an incubator cabinet) includes one or more windows and/or doors, that, when closed, are sealed to preserve sterility (e.g., after one or more chambers of the incubator have been sterilized). In some embodiments, each seal of the incubator is air tight up to a threshold level of pressure (e.g., up to 1 atm). In some embodiments, a gasket is provided to ensure a desired level of sealing capacity. In general, a "gasket" is understood as a mechanical seal that fills the space between two objects, generally to prevent leakage between the two objects while under compression. Gaskets are commonly produced by cutting from sheet materials, such as gasket paper, rubber, silicone, metal, cork, felt, neoprene, nitrile rubber, fiberglass, or a plastic polymer (such as polychlorotrifluoro-ethylene). It is often desirable that a gasket be made from a material that provides some degree of yielding such that it is able to deform and fill tightly the space it is designed for, including any slight irregularities. In some embodiments, gaskets can be used with an application of sealant directly to the gasket surface to function properly. In some embodiments, a gasket material can be a closed-cell neoprene foam which is non-reactant with carbon dioxide or ozone.

Internal Chambers

As used herein, an "internal chamber" is a chamber disposed in an incubator cabinet. An internal chamber may include one or more windows (e.g., optical windows made of glass, plastic, composite, or other substantially transparent material for viewing an area inside the incubator cabinet). An internal chamber may include at least one door (e.g., for permitting the transfer of items into or out of the internal chamber). In some embodiments, the at least one door may be disposed between the internal chamber and a transfer chamber. In certain embodiments, an interlock may prevent the door from opening at an undesirable time (e.g., when a portion of the incubator cabinet is open to the surrounding environment so that contaminants cannot enter the internal chamber). An internal chamber may be of any appropriate size and geometry. In some embodiments, an incubator cabinet may include more than one internal chamber. In other embodiments, an internal chamber may include one or more partitions to define different regions of an internal chamber. One or more internal chambers or partitions thereof may have different environmental conditions. The environment (e.g., air pressure, gas content, temperature, light, and humidity) inside an internal chamber may be measured and/or controlled by one or more meters, monitors, sensors, controls, pumps, valves, apertures, and/or light sources. In some embodiments, an internal chamber may have a gas-tight or hermetic seal, e.g., around one or more windows or doors. In particular embodiments, sealants such as grease and/or mechanical elements such as o-rings, gaskets, septa, KF, LF, QF, quick coupling, or other sealing mechanisms may be used to establish one or more gas-tight seals. In some embodiments, grooves, depressions, protrusions, and/or molded plastic elements may facilitate in establishing one or more gas-tight seals.

An internal chamber may be made of any useful material. In some embodiments, an internal chamber may include one or more plastics, polymers, metals, or glasses.

As used herein, a "door" is an element that permits communication between two or more environments or regions when opened and prevents communication between the two or more environments or regions when closed. A door may be of any type, such as a sliding door, pocket door, swinging door, hinged door, revolving door, pivot door, or folding door. The door may be manually, mechanically, or electrically operated. For example, an operator may open or close a door by manually grasping, pulling, pushing, and/or otherwise physically interacting with the door or an element thereof (e.g., a handle) or by operating a mechanical control (e.g., a button, toggle, spin-wheel, key, switch, cursor, screw, dial, screen, or touch-screen). In certain embodiments, a door may be controlled by electrical or digital controls, such as by a computer. A door may be an automatically opening door. For example, a door may include a sensor, such as a pressure, infrared, motion, or remote sensor that detects whether the door is open or closed and/or controls when the door opens or closes. A door may open by mechanical, pneumatic, electrical, or other means. In some embodiments, one or more doors may include one or more locking mechanisms. In particular environments, one or more doors may include one or more interlocks (e.g., a mechanical interlock such as a pin, bar, or lock or an electrical interlock such as a switch) to prevent one or more doors from opening at an undesirable time (e.g., when one or more chambers are open to the outside environment).

A transfer device for moving one or more items may be used to move items between the transfer chamber and the internal chamber. In some embodiments, the transfer device includes a conveyor belt or other similar device for maneuvering items. Non-limiting examples of items that can be moved by transfer devices include cell culture vessels, pipettes, containers, syringes, and other materials and instruments utilized in the culture of cells. In some embodiments, more than one transfer device may be included. In some embodiments, one or more transfer devices are located in the transfer chamber and/or in the internal chamber. In some embodiments, a transfer device may include one or more robotic elements. For example, a transfer device may include one or more robotic arms capable of gripping, lifting, pushing, grabbing, sliding, rotating, translating, releasing, raising, lowering, and/or tilting one or more items (e.g., pipettes).

In some embodiments, the transfer device is a cell culture vessel transfer device. As used herein, a "cell culture vessel transfer device" refers to a device that can transfer one or more cell culture vessels from a first location to a second location. In some embodiments, the transfer device is anchored within the internal chamber. In certain embodiments, the transfer device may transfer one or more items to or from multiple locations in an incubator cabinet. For example, a cell culture vessel transfer device may be used to move a cell culture vessel from a transfer chamber to an internal chamber, and/or from a storage location to an imaging location. In some embodiments, an incubator cabinet includes more than one transfer device, for moving one or more items (e.g., separate transfer devices for transferring items between and within chambers). A cell culture vessel transfer device may include one or more elements such as valves (e.g., electromagnetic or pneumatic valves), gears, motors (e.g., electrical or stepper motors), stages (e.g., xy or xyz stages), pistons, brakes, cables, ball-screw assemblies, rack-and-pinion arrangements, grippers, arms, pivot points, joints, translational elements, or other mechanical or electrical elements. In some embodiments, a cell culture vessel transfer device may include one or more robotic elements. For example, a cell culture vessel transfer device may include a robotic arm capable of gripping, lifting, pushing, grabbing, sliding, rotating, translating, releasing, raising, lowering, and/or tilting one or more cell culture vessels. In preferred embodiments, the cell culture vessel transfer device selectively and releasably grips one or more cell culture vessels. In certain embodiments, a cell culture vessel transfer device may include an arm coupled to a mechanical gripper. For example, an arm may include a mechanical gripper at or near one end for releasably gripping a cell culture vessel and be securely coupled to a surface or element of the incubator at or near the other end. In some embodiments, a robotic arm includes a pivot point where the mechanical gripper couples to the arm and one or more pivot and/or translational joints along the arm to permit flexible rotation and translation of a portion of the arm. In this manner, a robotic arm may access one or more cell culture vessels at different horizontal and vertical positions within an incubator cabinet (e.g., within a storage array in an internal chamber).

In some embodiments, a cell culture vessel transfer device is an automated transfer device. For example, the automated transfer device may be a robotic arm controlled by a computer that is programmed to move cell culture vessels from a storage location within the internal chamber of the incubator to an imaging location within the internal chamber of the incubator. In some embodiments, a cell culture vessel transfer device is manually operated. For example, a robotic arm located inside the internal chamber of an incubator may be operated by a user-controlled joystick from a location outside of the internal chamber of the incubator in order to move cell culture vessels from a storage location within the internal chamber of the incubator to an imaging location within the internal chamber of the incubator.

As used herein, a "storage location" refers to a location at which one or more cell culture vessels is stored (e.g., within an incubator cabinet). For example, one or more cell culture vessels may be stored at a storage location and later transferred to a different location (e.g., an imaging location). The storage location may be disposed in the internal chamber of the incubator cabinet. A storage location may be configured for storing a plurality of cell culture vessels. For example, a storage location may include one or more storage arrays, racks, shelves, pigeon-holes, cubbies, trays, slots, or other positions or mechanisms. In some embodiments, a storage location may be configured to store cell culture vessels horizontally, while in other embodiments it may be configured to store cell culture vessels vertically. For example, a storage location may include a plurality of slots to receive cell culture vessels stacked vertically over one another. A storage location may be configured to hold 1, 2, 3, 4, 5, 6, 7, 8, 9, 10, 15, 20, 25, 30, 35, 40, 45, 50, 100, or any other number of cell culture vessels. In some embodiments, a storage location may be configured to hold greater than 100 cell culture vessels. In some embodiments, each cell culture vessel in a storage location houses cells from a different subject. In some embodiments, a storage location may include a mechanism for moving one or more storage arrays, racks, shelves, pigeon-holes, cubbies, trays, slots, or other positions or mechanisms. For example, a storage location may include one or more motors and movable stages (e.g., an xy or xyz stage) to move a storage rack from one position in an internal chamber to another position in an internal chamber, e.g., to facilitate access to one or more cell culture vessels stored in different locations. In some embodiments, the incubator cabinet may include one or more cell culture vessel transfer devices for moving one or more cell culture vessels.

A storage location may be configured to securely hold or receive one or more cell culture vessels. For example, one or more components of the storage location may include one or more locking mechanisms that have one or more adhesive, magnetic, electrical, and/or mechanical components (e.g., snaps, fasteners, locks, clasps, gaskets, o-rings, septa, springs, and other engagement members). In some embodiments, a storage location and/or cell culture vessel may include one or more grooves or depressions and/or may involve pieces of molded plastic. For example, a cell culture vessel may include one or more protruded features (e.g., a rim or knob) that is molded for insertion into one or more corresponding grooves, holes, or depressions at a storage location. In some cases, a cell culture vessel may include one or more grooves, holes, or depressions that are molded to fit one or more corresponding protruded features at a storage location.

As used herein, an "imager" refers to an imaging device for measuring light (e.g., transmitted or scattered light), color, morphology, or other detectable parameters such as a number of elements or a combination thereof. An imager may also be referred to as an imaging device. In certain embodiments, an imager includes one or more lenses, fibers, cameras (e.g., a charge-coupled device camera or CMOS camera), apertures, mirrors, filers, light sources (e.g., a laser or lamp), or other optical elements. An imager may be a microscope. In some embodiments, the imager is a bright-field microscope. In other embodiments, the imager is a holographic imager or microscope. In other embodiments, the imager is a fluorescence microscope.

As used herein, a "fluorescence microscope" refers to an imaging device which is able to detect light emitted from fluorescent markers present either within and/or on the surface of cells or other biological entities, said markers emitting light at a specific wavelength in response to the absorption a light of a different wavelength.

As used herein, a "bright-field microscope" is an imager that illuminates a sample and produces an image based on the light absorbed by the sample. Any appropriate bright-field microscope may be used in combination with an incubator cabinet provided herein.

As used herein, a "holographic imager" is an imager that provides information about an object (e.g., sample) by measuring both intensity and phase information of electromagnetic radiation (e.g., a wave front). For example, a holographic microscope measures both the light transmitted after passing through a sample as well as the interference pattern (e.g., phase information) obtained by combining the beam of light transmitted through the sample with a reference beam.

A holographic imager may also be a device that records, via one or more radiation detectors, the pattern of electromagnetic radiation, from a substantially coherent source, diffracted or scattered directly by the objects to be imaged, without interfering with a separate reference beam and with or without any refractive or reflective optical elements between the substantially coherent source and the radiation detector(s).

In some embodiments, an incubator cabinet includes a single imager. In some embodiments, an incubator cabinet includes two imagers. In some embodiments, the two imagers are the same type of imager (e.g., two holographic imagers or two bright-field microscopes). In some embodiments, the first imager is a bright-field microscope and the second imager is a holographic imager. In some embodiments, an incubator cabinet comprises more than 2 imagers. In some embodiments, cell culture incubators comprise three imagers. In some embodiments, cell culture incubators having 3 imagers comprise a holographic microscope, a bright-field microscope, and a fluorescence microscope.

As used herein, an "imaging location" is the location where an imager images one or more cells. For example, an imaging location may be disposed above a light source and/or in vertical alignment with one or more optical elements (e.g., lens, apertures, mirrors, objectives, and light collectors).

As used herein, a "fiducial mark" refers to a feature that facilitates alignment of one or more components. In some embodiments, fiducial marks may include one or more hole apertures over a fluorescent media or printed or embossed fluorescent material. In other embodiments, fiducial marks may include grids, lines, or symbols. In some embodiments, one or more cell culture vessels include one or more fiducial marks to facilitate alignment of one or more cell culture vessels with an imager. In some embodiments, fiducial marks may be associated with moving parts, including transfer devices and robotics devices.

In some embodiments, a cell culture vessel is substantially aligned with an imager. In some embodiments, a cell culture vessel is substantially aligned with an imager via the use of at least one fiducial mark. As used herein, the term "substantially aligned" implies that one or more elements are substantially overlapping, identical, and/or in line with one another. The substantial alignment of one or more cell culture vessels at one or more locations (e.g., imaging locations) may facilitate the analysis of a sample by permitting overlapping images of the cell culture vessel to be obtained. For example, a cell culture vessel may be imaged at a first imaging location by a first imager and subsequently imaged at a second imaging location by a second imager. If the imaging fields of the respective imagers are substantially aligned, the images recorded by the first and second imagers may be combined ("stitched together") for analysis. One or more fiducial marks present on one or more cell culture vessels may facilitate substantial alignment. In some cases, one or more fiducial marks present at one or more imaging or other locations (e.g., manipulation or maintenance locations) may facilitate substantial alignment.

As used herein, a "manipulator for manipulating cells" refers to a device for manipulating cells in the internal chamber. The manipulator may include one or more needles, capillaries, pipettes, and/or micromanipulators. For example, the manipulator may include a cell picker. A manipulator for manipulating cells may operate by detecting desirable cells or groups thereof present at a first location based on a predetermined criterion and transferring the desired cells or groups thereof from the first location to a second location. A cell picker may detect, pick, and/or transfer desirable or undesirable (e.g., pre-differentiated cell weeding) cells or groups thereof based on a manual or automated analysis. In some embodiments, information produced by an imager may be analyzed to detect desirable or undesirable cells. The cell picker may then transfer the desirable or undesirable cells to the second location. For example, an imager may image cells in or on a cell culture vessel at an imaging location, and the image used to identify desirable or undesirable cells or groups thereof. The cell picker may then transfer the desirable or undesirable cells, e.g., by contacting each desired cell or cells with a needle, capillary, pipette, or micromanipulator and effecting a movement of the cell or cells, from their first location to a second location in or on the cell culture vessel or elsewhere in the internal chamber. In some embodiments, the first location of the cells may be in or on a cell culture vessel. In particular embodiments, a cell picker transfers cells from a first location in or on a cell culture vessel to a second location on the same cell culture vessel. In other embodiments, a cell picker transfers cells from a first location in or on a first cell culture vessel to a second location in or on a second cell culture vessel. In certain other embodiments, a cell picker transfers cells from a first location in or on a cell culture vessel to a second location in the internal chamber that is not in or on a cell culture vessel.

In some embodiments, the manipulator includes at least one microelectrode. As used herein, the term "microelectrode" refers to an electrical conductor used to deliver electrical stimulation to a cell. For example, microelectrodes can be used to deliver genetic material into a cell by electroporation. In some embodiments, the manipulator includes at least one microinjector. Generally, microinjectors are glass micropipettes that have been pulled to form a sharp, hollow structure capable of piercing the membrane of a cell and serving as a conduit for the introduction of genetic material into the cell. In some embodiments, cell cultures are manipulated in other ways during culture in incubators and vessels described herein. For example, cell cultures may be transfected with nucleic acids (e.g., DNA or RNA) or exposed to viral infection (e.g., using recombinant virus particles to deliver DNA or RNA).

In some embodiments, a manipulator includes fluid handling devices. For example, a manipulator may include one or more liquid dispensing apparatus, such as pipette tip holders or a cell printing device. In some embodiments fluid handling devices are automated. In some aspects, manipulators having automated fluid handling systems that dispense growth media from fluid storage vessels located inside the internal chamber of the incubator to cell culture vessel can be used.

In some embodiments (e.g., for adherent cell cultures), culture media can be removed directly by aspiration and replaced with fresh media. In some embodiments (e.g., for non-adherent/suspension cultures), media changes can involve centrifuging a cell culture, removing the old culture media and replacing it with fresh media. In some embodiments, the centrifuge is located in the internal chamber of an incubator. In some embodiments, culture vessels allow for continuous media replacement. In some embodiments, the incubators described herein may include one or more components that can be used to process, replace, supply, and/or maintain different aspects of a culture media to support cells. Incubators may include a reservoir containing waste media and/or a reservoir containing fresh media. Such reservoirs may be present (e.g., for temporary storage) within a refrigerator inside the incubator or a refrigerated section of the incubator. In some embodiments, one or more reservoirs are provided outside the incubators and piping is provided into and out from the incubator space to supply or draw from a liquid handler units (e.g., liquid handle units having an aspirator) or temporary reservoir within the incubator to facilitate cells feeding, media changes, and other related needs. For suspension cells, devices may be provided within the incubator to separate cells from waste media (e.g., centrifuge(s) to facilitate cell pelleting) to facilitate automated media changes as part of an incubator provided herein. In some embodiments, the document provides a system comprising a cell culture incubator connected to a computer, capable of automatically monitoring and adjusting cell culture conditions for optimal growth of the cell culture.

In some embodiments, cells are passaged within an incubator described herein. In some embodiments, a cell culture is split, and a subset of the cell culture is transferred to a fresh culture vessel for further growth. In some embodiments (e.g., for adherent cell cultures), cells are detached (e.g., mechanically, for example, using gentle scraping, and/or enzymatically, for example, using trypsin-EDTA or one or more other enzymes) from a surface prior to being transferred to a fresh culture vessel. In some embodiments (e.g., for suspension cell cultures), a small volume of a cell culture is transferred to a fresh culture vessel.

In some embodiments, a manipulator is manually operated. For example, a manipulator having a fluid handling system located inside the internal chamber of an incubator cabinet may be electronically-linked to and controlled by a user-directed joystick located outside the internal chamber of the incubator cabinet. In some embodiments, the user-directed joystick is connected to a display device. In some embodiments, the display device shows images captured by an imaging device inside the internal chamber of the incubator cabinet.

In some embodiments, a manipulator is automated. For example, a manipulator inside an internal chamber of an incubator cabinet may be electronically connected to a controller outside of the incubator cabinet that directs the manipulator. In some embodiments, the computer automatically remembers where particular cell culture vessels are located inside the incubator. In some embodiments, the computer uses barcodes or other identifying information to verify that the said locations are correctly remembered.

One or more elements of the manipulator for manipulating cells may be sterilized, for example using a sterilizing composition or method (e.g., ethanol or ozone gas), prior to manipulation.

As used herein, "manipulation location" refers to the location at which cells are manipulated by a manipulator for manipulating cells (e.g., a cell picker). In certain embodiments, the manipulation location may be the same as the imaging location.

According to one aspect, the cell culture incubator includes an incubator cabinet with an imaging location and a manipulating location. Cells of a cell culture vessel are imaged at the imaging location by an imager and manipulated at the manipulating location by a manipulator. In some embodiments, the imaging location and the manipulating location are two distinct locations within the incubator cabinet. The cell culture incubator may include a transfer device that moves cell culture vessels between the imaging location and the storage location. In other embodiments, the imaging location and the manipulating location are the same, such that the cells of culture vessels are imaged at the manipulation location.

In some embodiments, an imager may be used in conjunction with a manipulator. For example, an imager may image cells in or on a cell culture vessel at an imaging location, and the image used to identify desirable cells or groups thereof. The manipulator may then transfer the desirable cells, e.g., by contacting each desired cell or cells with a needle, capillary, pipette, or micromanipulator and effecting a movement of the cell or cells, from their first location to a second location in or on the cell culture vessel or elsewhere in the internal chamber. In some embodiments, the manipulator aseptically transfers growth media, growth factors, or expression vectors into cell culture vessels.

In some embodiments, a single location within the incubator cabinet may serve as an imaging location and a manipulating location. In some embodiments, an imaging location and a manipulating location are at different locations within the incubator cabinet. In one embodiment, cells are imaged as they are manipulated by the manipulator.

In some embodiments, the environment inside an incubator is controlled by a control system that may be configured to control the temperature, humidity, carbon dioxide, oxygen and other gaseous components ((e.g., sterilization gases, such as, ozone, and hydrogen peroxide)) inside the incubator (e.g., in one or more internal chambers). In some embodiments, a control system controls the environmental conditions (e.g., temperature, humidity, carbon dioxide, oxygen and other gaseous components) within each internal chamber separately. For example, in order to protect sensitive mechanical, electronic and optical components, the humidity of an internal chamber may be maintained at a lower level than an internal chamber having a storage location. In some embodiments, the incubator is further provided with a monitoring system with predefined sensors. Examples of monitoring devices include but are not limited to oxygen monitors, carbon dioxide monitors, ozone gas detectors, hydrogen peroxide monitors and multi gas monitors. For example, in some embodiments, an incubator advantageously includes a plurality of sensors responsive to different parameters relevant to cell growth, which may include temperature, air purity, contaminant levels, pH, humidity, $N_2$, $CO_2$, $O_2$ and light. By means of this monitoring system, parameters in the incubator can be measured using sensors for the duration of a culture or process. In some embodiments, parameters measured by the sensors are transmitted by the monitoring system via a line to a computer-controlled monitoring and control system for further processing as discussed elsewhere herein.

In some embodiments, an environmental monitoring system can be used in conjunction with an incubator described herein. In some embodiments, one or more sensors that provide for the measurement of temperature, air composition (e.g., $CO_2$ concentration, $O_2$ concentration, etc.), and/or humidity of the system can be associated with an incubator (e.g., fitted within an incubator cabinet). In some embodiments, one or more such sensors can be incorporated as part of an incubator (e.g., attached to, integral to, or otherwise connected to an internal wall or door of the incubator). In some cases, one or more sensors can be positioned at any suitable location(s) outside or inside an incubator cabinet (e.g., within a transfer chamber and/or an internal chamber, for example attached to an internal wall, and/or upper or lower internal surface).

In some embodiments, a gas sensor is provided that can provide a reading in real time of the concentration of gas in contact with the sensor (e.g., gas in a cabinet, or ambient air) in percent, parts per million, or any other standard unit. Gas sensors for use in the methods and incubators provided herein include $CO_2$ sensors, $O_2$ sensors, $N_2$ sensors, ozone gas detectors, hydrogen peroxide monitors, multi gas monitors, and CO sensors. Such sensors are available from a number of commercial sources. In some cases, the environment of the incubator may be modulated or controlled based upon the information provided by the sensors described herein. For example, the level of $CO_2$ in an incubator may be increased upon indication from a $CO_2$ sensor that a lower than desirable concentration of $CO_2$ is present in the incubator.

In some embodiments, one or more heating or cooling elements can be incorporated within the incubator (e.g., on an inner surface of the cabinet or door, and/or integrated within one or more of the walls and/or the base of the cabinet) for purposes of controlling the temperature within the incubator. In some embodiments, a heating element can be used for thawing liquids, for example, cell culture media or other reagents.

In some embodiments, one or more air or oxygen sources, carbon filters, and/or one or more humidification or dehumidification systems are connected to the incubator and configured to control the level of oxygen, carbon dioxide, and/or humidity within the incubator (e.g., in response to signals from the one or more sensors in or attached to the incubator). In some embodiments, one or more controllers are attached to the sensors and other systems to control the internal environment of the incubator.

In some embodiments, an incubator can include one or more light sources (e.g., an incandescent bulb, LED, UV, or other light source). These can be placed within the incubator to illuminate regions within the cabinet. In some embodiments, the culture system operation is monitored using a camera or other light sensitive device that can be placed within or outside the incubator. In some embodiments, the light source is a sterilizing light source. For example, a UV lamp may be located within the transfer chamber and/or the interior chamber of an incubator provided herein.

In some embodiments, the incubator includes a transparent object (e.g., window) that allows visible light or other light wavelengths from within the incubator to be detected by a camera or other light sensitive device placed outside the incubator. In some embodiments, the inner surface of the transparent object can be wiped (e.g., from the inside of the cabinet) to prevent or remove condensation droplets that may accumulate (e.g., due to the humid air inside the incubator) on the inner surface and interfere with the monitoring of the system. In some embodiments, the surface can be wiped by a wiper that is automatically controlled by a controller.

In some embodiments, a sensor or other feature is provided to detect when one or more doors of an incubator are opened (e.g., when an incubator cabinet door, such as an external or internal door, is opened). Such features are useful because they allow operators to keep track of or be warned of any unscheduled or unauthorized openings of the incubator (e.g., the incubator cabinet) that could jeopardize sterility, spoil a production, compromise an assay or experiment, etc.

In some embodiments, a radiofrequency beacon or other signal source is located within the incubator (e.g., within the incubator cabinet) that can be used to determine the location of one or more devices within the incubator cabinet (e.g., devices having sensors that can detect the signal and use it to determine their location). In some embodiments, the devices could have signal sources and the sensor(s) could be located within one or more of the chambers of an incubator cabinet (e.g., located on an internal surface of an internal chamber).

In some embodiments, light signals or lasers (e.g., a grid of laser signals) can be used to determine the location and/or identity of one or more devices or components within the incubator cabinet. Such information can be communicated, e.g., wired or wirelessly, to an external computer or monitoring station. The information can be used to control operation of a transfer device, e.g., a robotic arm, within the incubator cabinet to ensure that the transfer device can grab, manipulate, or maneuver devices or items appropriately within the incubator cabinet.

In some embodiments, before containers or vessels are brought into an incubator cabinet, a user can select an automation system protocol based on the particular containers, vessels, ingredients, or cells that are being inserted into the incubator cabinet. Relevant information related to the incubator and/or one or more incubator components, and the cells being grown can be entered into a data system. For example, one or more identifiers such as barcodes (e.g., 1D or 2D barcodes) can be placed on the container or vessel and other significant information, such as, the type of container, the contents of the container and, what assays or manipulations are to be performed on the sample in the container can be specified. In some embodiments, information related to the incubator system and/or cells can be contained in one or more barcodes, on a separate data system, or a combination thereof. The user may also enter information that identifies the dimensionality (e.g., height, diameter) of the vessel or other container or the system itself determine measure the height of the vessel or other container. Using this information, the robotic arm may be requested to transport a particular container, such as when an analytical module is ready to perform an assay or other manipulation on cells grown in the vessels or has completed performing an assay or manipulation.

Computer and Control Equipment

The incubators provided herein include several components, including sensors, environmental control systems, robotics, etc. which may operate together at the direction of a computer, processor, microcontroller or other controller. The components may include, for example, a transfer device (e.g., robotic arm), a liquid handling devices, a delivery system for delivering culture vessels, or other components to or from the incubator cabinet, an environmental control system for controlling the temperature and other environmental aspects of the incubator cabinet, a door operation system, an imaging or detection system, and a cell culture assay system.

In some cases, operations such as controlling operations of a cell culture incubator and/or components provided therein or interfacing therewith may be implemented using hardware, software or a combination thereof. When implemented in software, the software code can be executed on any suitable processor or collection of processors, whether provided in a single component or distributed among multiple components. Such processors may be implemented as integrated circuits, with one or more processors in an integrated circuit component. A processor may be implemented using circuitry in any suitable format.

A computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable, mobile or fixed electronic device, including the incubator itself.

In some cases, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. In other examples, a computer may receive input information through speech recognition or in other audible format, through visible gestures, through haptic input (e.g., including vibrations, tactile and/or other forces), or any combination thereof.

One or more computers may be interconnected by one or more networks in any suitable form, including as a local area network or a wide area network, such as an enterprise network or the Internet. Such networks may be based on any suitable technology and may operate according to any suitable protocol and may include wireless networks, wired networks, or fiber optic networks.

The various methods or processes outlined herein may be coded as software that is executable on one or more processors that employ any one of a variety of operating systems or platforms. Such software may be written using any of a number of suitable programming languages and/or programming or scripting tools, and may be compiled as executable machine language code or intermediate code that is executed on a framework or virtual machine.

One or more algorithms for controlling methods or processes provided herein may be embodied as a readable storage medium (or multiple readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other tangible storage medium) encoded with one or more programs that, when executed on one or more computers or other processors, perform methods that implement the various methods or processes described herein.

In some embodiments, a computer readable storage medium may retain information for a sufficient time to provide computer-executable instructions in a non-transitory form. Such a computer readable storage medium or media can be transportable, such that the program or programs stored thereon can be loaded onto one or more different computers or other processors to implement various aspects of the methods or processes described herein. As used herein, the term "computer-readable storage medium" encompasses only a computer-readable medium that can be considered to be a manufacture (e.g., article of manufacture) or a machine. Alternatively or additionally, methods or processes described herein may be embodied as a computer readable medium other than a computer-readable storage medium, such as a propagating signal.

The terms "program" or "software" are used herein in a generic sense to refer to any type of code or set of executable instructions that can be employed to program a computer or other processor to implement various aspects of the methods or processes described herein. Additionally, it should be appreciated that according to one aspect of this embodiment, one or more programs that when executed perform a method or process described herein need not reside on a single computer or processor, but may be distributed in a modular fashion amongst a number of different computers or processors to implement various procedures or operations.

Executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in computer-readable media in any suitable form. Non-limiting examples of data storage include structured, unstructured, localized, distributed, short-term and/or long term storage. Non-limiting examples of protocols that can be used for communicating data include proprietary and/or industry standard protocols (e.g., HTTP, HTML, XML, JSON, SQL, web services, text, spreadsheets, etc., or any combination thereof). For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags, or other mechanisms that establish relationship between data elements.

In some embodiments, information related to the operation of the incubator (e.g., temperature, humidity, gas composition, images, cell culture conditions, etc., or any combination thereof) can be obtained from one or more sensors associated with the incubator (e.g., located within the incubator cabinet, or located within the incubator but outside the incubator cabinet), and can be stored in computer-readable media to provide information about conditions during a cell culture incubation. In some embodiments, the readable media comprises a database. In some embodiments, said database contains data from a single incubator. In some embodiments, said database contains data from a plurality of incubators. In some embodiments, data is stored in a manner that makes it tamper-proof. In some embodiments, all data generated by the instrument (e.g., an incubator) is stored. In some embodiments, a subset of data is stored.

In some embodiments, the component (e.g., a computer) controls various processes performed inside the incubator. For example, a computer may direct control equipment (e.g., a manipulator, an imager, a fluid handling system, etc.). In some embodiments, the computer controls imaging of cell cultures, picking of cells, weeding of cells (e.g., removal of cell clumps), monitoring of cell culture conditions, adjustment of cell culture conditions, tracking of cell culture vessel movement within the incubator, and/or scheduling of any of the foregoing processes.

Turning to the figures, FIG. 1 shows a schematic of an illustrative embodiment of a cell culture system. In some embodiments, a cell culture system includes an incubator cabinet having an external door (100) which opens into an internal chamber (101). Inside the internal chamber are a plurality cell culture vessels (102), each vessel having a passage configured to permit materials to be aseptically passed into or out from the vessel; each cell culture vessel (P1, P2, P3, P4, P5, and P6) may contain a cell sample from a different subject.

Figure 2A:
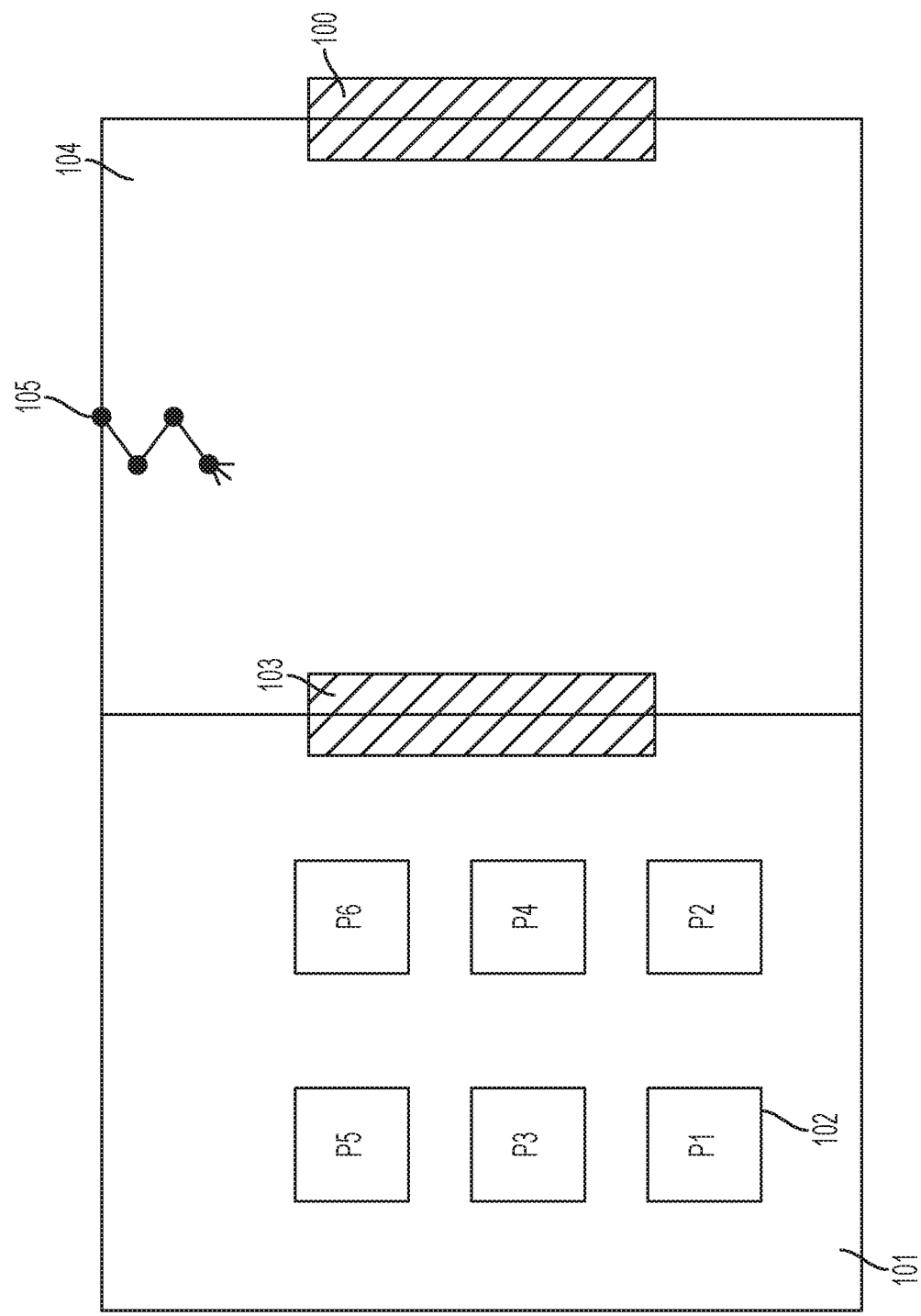
FIGS. 2A-2B are schematics of illustrative embodiments of cell culture systems.
Figure 2B:
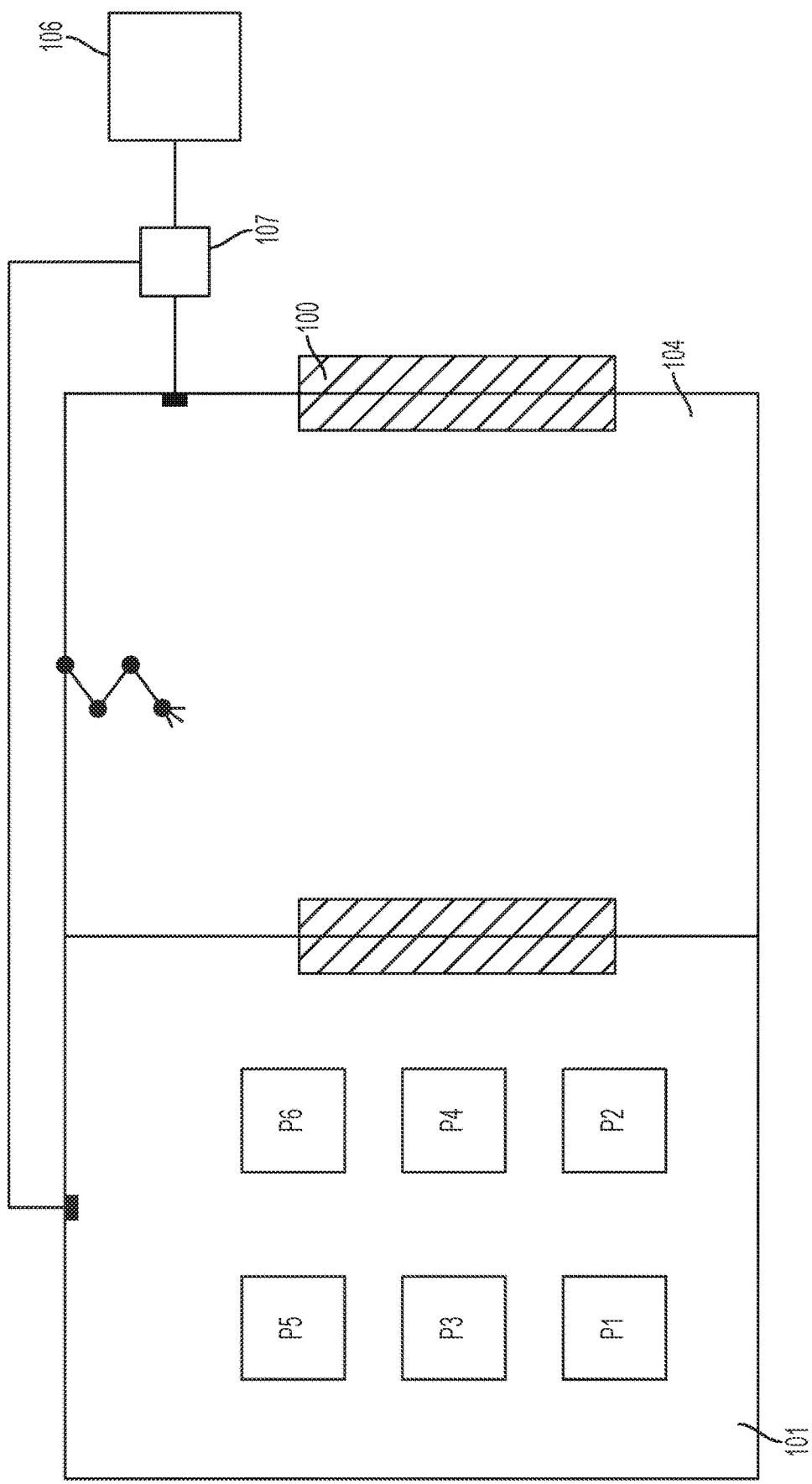

FIGS. 2A-2B show schematics of illustrative embodiments of a cell culture systems. FIG. 2A depicts a cell culture system including an incubator cabinet having an internal chamber (101) housing a plurality of cell culture vessels (102), each vessel having a passage configured to permit materials to be aseptically passed into or out from the vessel; an internal door (103), which opens into a transfer chamber (104), and forms a gas-tight seal when closed; a cell culture vessel transfer device (105); and, an external door (100) that connects the transfer chamber to the exterior of the incubator cabinet when open. FIG. 2B depicts a schematic of the cell culture system embodied in FIG. 2A, further including an ozone generator (106) and a pump (107). In some embodiments, the ozone generator and pump are in fluid communication. In some embodiments, the ozone generator and the incubator cabinet are in fluid communication. For example, the ozone generator can be in fluid communication with the internal chamber and/or the transfer chamber of the incubator cabinet via a pipe or tubing connected to an inlet or outlet of the incubator cabinet. In some embodiments, the pump and the incubator cabinet are in fluid communication. For example, the pump can be in fluid communication with the internal chamber and/or the transfer chamber of the incubator cabinet via a pipe or tubing connected to an inlet or outlet of the incubator cabinet. In some embodiments, the pump is used to remove ozone gas from the internal chamber and/or transfer chamber of the incubator cabinet.

Figure 3:
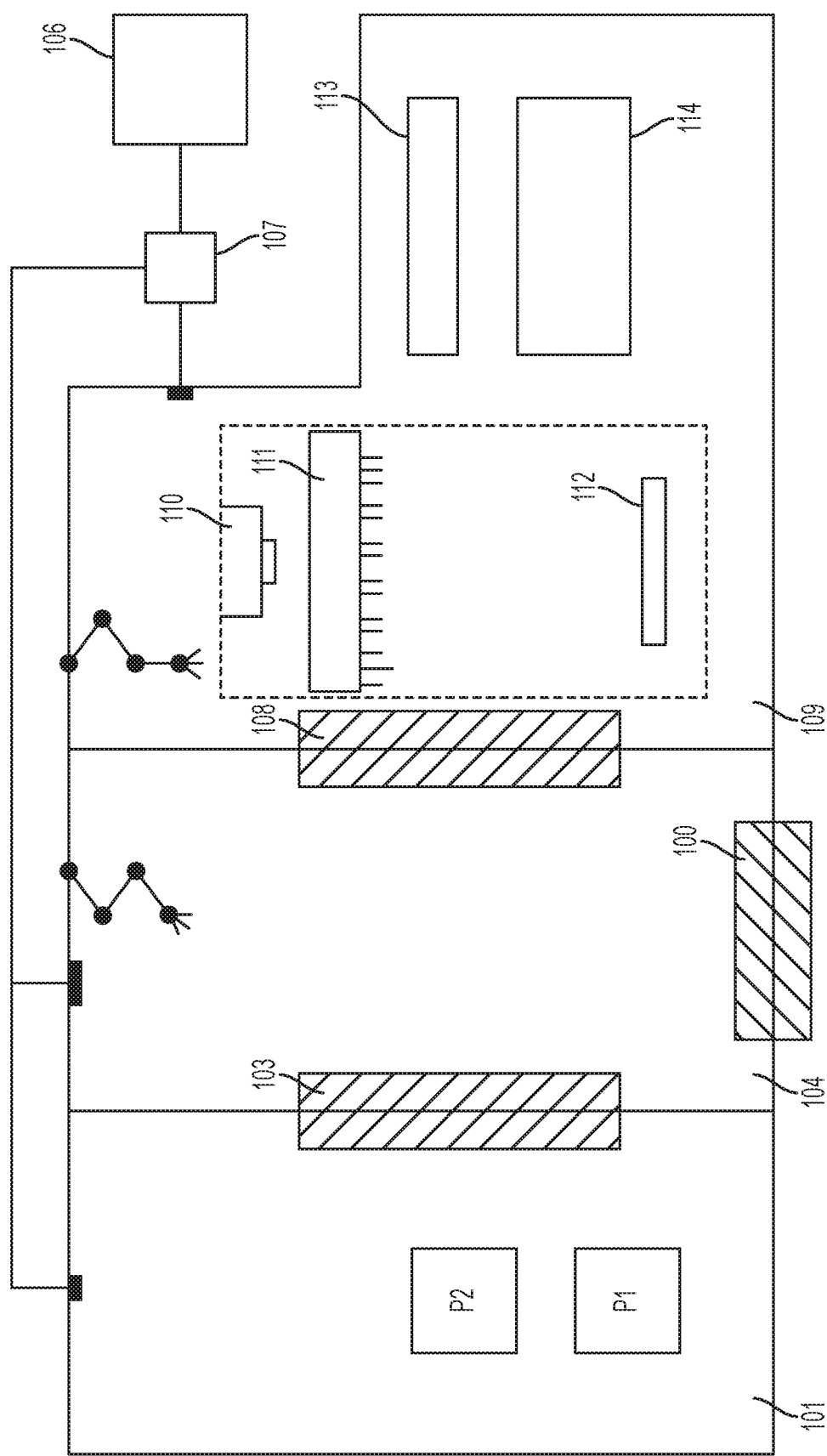
FIG. 3 is a schematic of an illustrative embodiment of a cell culture system comprising an incubator cabinet comprising a transfer cabinet, a first internal chamber containing a plurality of cell culture vessels, and a second internal chamber comprising an imager and a manipulator.

FIG. 3 shows a schematic of an illustrative embodiment of a cell culture system. In some embodiments, the cell culture system includes an incubator cabinet having an external door (100), which opens into a transfer chamber (104). The transfer chamber has two internal doors (103, 108). The first internal door (103) opens into a first internal chamber (101), which houses a plurality of cell culture vessels, each vessel having a passage configured to permit materials to be aseptically passed into or out from the vessel. The second internal door (108) opens into a second internal chamber (109). The second internal chamber includes an imager (110), a manipulator (111) and a manipulation location (112). In some embodiments, the second internal chamber also includes a fluid reservoir (113) and/or a centrifuge (114). In some embodiments, the second internal chamber includes a FACS machine.

Figure 4:
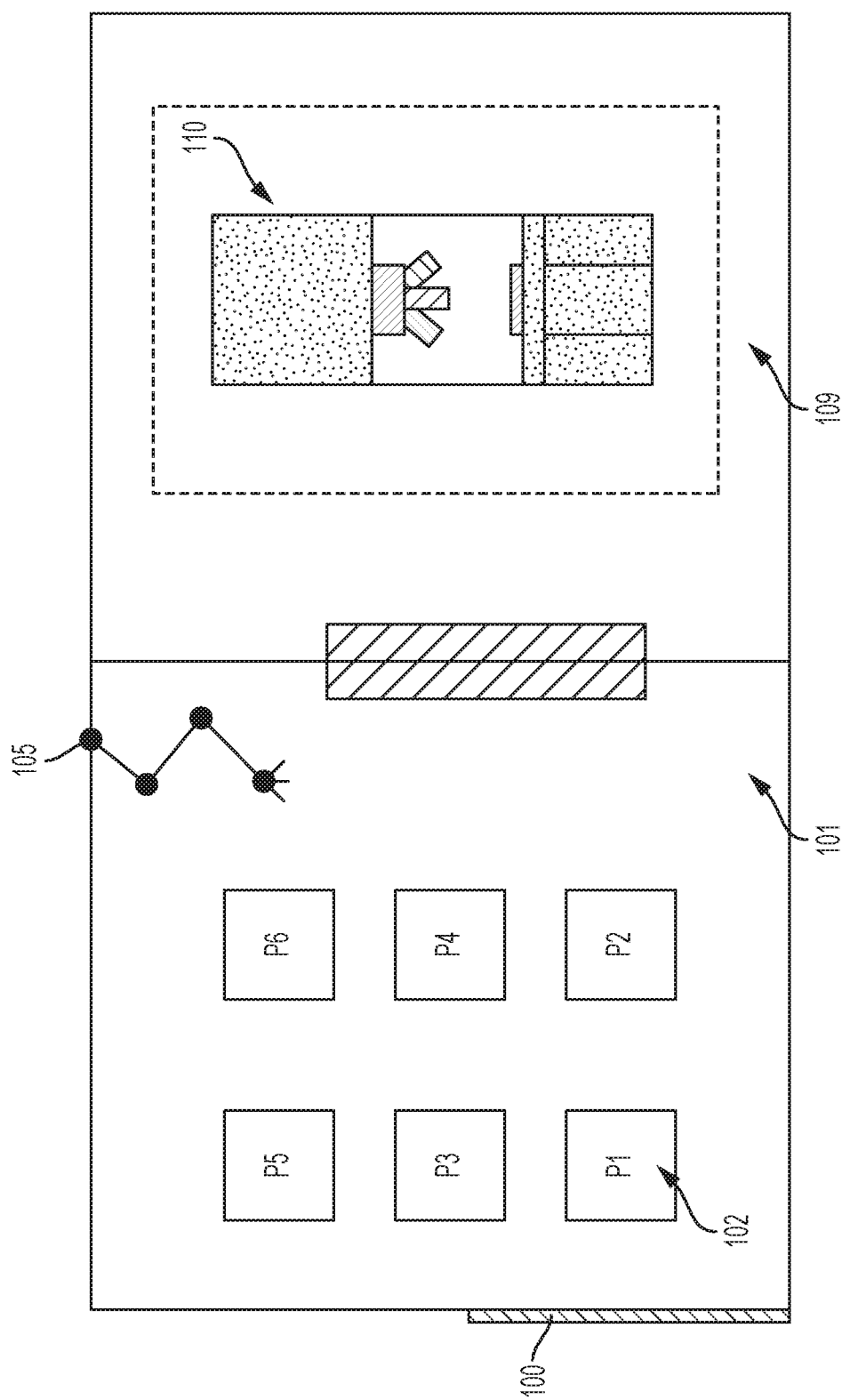
FIG. 4 is a schematic of an illustrative embodiment of a cell culture system comprising an incubator cabinet comprising an internal chamber, a plurality of cell culture vessels, and an imager.

FIG. 4 shows a schematic of an illustrative embodiment of a cell culture system. In some embodiments, the incubator cabinet includes an external door (100) that opens into a first internal chamber (101), which houses a plurality of cell culture vessels, each vessel configured to permit materials to be aseptically passed into or out from the vessel, the incubator cabinet includes a transfer device (105). An internal door connects the first internal chamber to a second internal chamber (109), that includes an imager (110).

The above aspects and embodiments may be employed in any suitable combination, as the present invention is not limited in this respect.

It should be understood that aspects of the invention are described herein with reference to certain illustrative embodiments and the figures. The illustrative embodiments described herein are not necessarily intended to show all aspects of the invention, but rather are used to describe a few illustrative embodiments. Thus, aspects of the invention are not intended to be construed narrowly in view of the illustrative embodiments. In addition, it should be understood that aspects of the invention may be used alone or in any suitable combination with other aspects of the invention.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A cell culture incubator comprising:
    a transfer chamber;
    first and second internal chambers, each having a controlled temperature and gas mixture therein appropriate for the growth of a type of cell for incubation of said type of cell in one or more cell culture vessels in the internal chambers, wherein the first internal chamber comprises a storage location for storing a plurality of cell culture vessels and wherein the second internal chamber comprises at least one imager;
    an external door opening from an external environment to the transfer chamber;
    a first internal door opening from the transfer chamber to the first internal chamber;
    a second internal door opening from the transfer chamber to the second internal chamber, wherein the first internal door and the second internal door each forms a substantially gas-tight seal when closed;
    an interlock for preventing the first and second internal doors from opening when the external door is open;
    an automated transfer device for moving at least one of the plurality of cell culture vessels between the storage location in the first internal chamber and the at least one imager in the second internal chamber, wherein the transfer device includes at least one robotic element in at least one of the chambers and wherein the storage location is configured to automatically move the at least one of the plurality of cell culture vessels into a position to be transferred by the automated transfer device;
    at least one processor configured to control the movement of the at least one of the plurality of cell culture vessels in the storage location and the transfer of the at least one of the plurality of cell culture vessels to and from the storage location; and
    radiofrequency sensors for sensing the position of each cell culture vessel in the chambers of the incubator and communicating with the at least one processor to enable the at least one processor to determine the location of each cell culture vessel for desired transfer of each cell culture vessel between the storage location and the at least one imager.

2. The cell culture incubator according to claim 1, wherein the storage location is configured to receive the at least one of the plurality of cell culture vessels transferred by the automated transfer device and move the at least one of the plurality of cell culture vessels into storage.

3. The cell culture incubator according to claim 2, wherein the storage location has at least one movable stage to move a cell culture vessel in storage in x-axis, y-axis and z-axis directions to effect transfer to the at least one imager and storage when returned from the at least one imager.

4. The cell culture incubator according to claim 1, wherein the plurality of cell culture vessels has fiducial marks and wherein the at least one imager uses the fiducial marks to align a cell culture vessel for imaging.

5. The cell culture incubator according to claim 1, wherein the radiofrequency sensors include radiofrequency beacons in the incubator.

6. The cell culture incubator according to claim 1, wherein the radiofrequency sensors sense light signals in the incubator.

7. The cell culture incubator according to claim 1, wherein cell culture vessels include bar codes encoding bar code data and the incubator includes a bar code reader for reading the bar codes and wherein the at least one processor receives the bar code data to enable a user to select a system protocol based at least in part on the bar code data to determine operations to be performed on cells in the corresponding cell culture vessel.

8. The cell culture incubator according to claim 1, further comprising an ozone generator coupled to a pump, wherein the ozone generator is configured for supplying ozone gas to the transfer chamber.

9. The cell culture incubator according to claim 1, wherein the external door forms a substantially gas-tight seal when closed.

10. The cell culture incubator according to claim 1, wherein each cell culture vessel of the plurality of cell culture vessels is tagged with a unique barcode and wherein the incubator further comprises a bar code reader for reading each unique barcode.

* * * * *